United States Patent
Nardella et al.

[11] Patent Number: 6,080,152
[45] Date of Patent: Jun. 27, 2000

[54] ELECTROSURGICAL INSTRUMENT

[75] Inventors: Paul C. Nardella, Wareham; Thomas A. Wrublewski, Sharon, both of Mass.; Piush Vidyarthi, San Francisco, Calif.; Trinh N. Nguyen, Foster City, Calif.; Dai T. Ton, Milpitas, Calif.; Steven Bacich, Half Moon Bay, Calif.

[73] Assignees: Medical Scientific, Inc., Taunton, Mass.; Conceptus, Inc., San Carlos, Calif.

[21] Appl. No.: 09/092,694

[22] Filed: Jun. 5, 1998

[51] Int. Cl.⁷ .................................................. A61B 18/14
[52] U.S. Cl. ............................ 606/46; 606/48; 606/49; 606/50; 607/147
[58] Field of Search ................................. 606/41, 45, 46, 606/49, 50; 607/147; 601/20

[56] References Cited

U.S. PATENT DOCUMENTS

| | | | |
|---|---|---|---|
| Re. 33,925 | 5/1992 | Bales et al. ............................... | 606/48 |
| 4,202,338 | 5/1980 | Bitrolf ...................................... | 128/303.15 |
| 4,311,143 | 1/1982 | Komiya ................................... | 128/303.15 |
| 4,362,160 | 12/1982 | Hiltebrandt ............................. | 128/303.15 |
| 4,493,320 | 1/1985 | Treat ........................................ | 128/303.15 |
| 4,532,924 | 8/1985 | Auth et al. ............................... | 128/303.17 |
| 4,657,017 | 4/1987 | Sorochenko ............................ | 128/303.14 |
| 4,802,476 | 2/1989 | Noerenberg et al. ................... | 128/303.14 |
| 4,905,691 | 3/1990 | Rydell ..................................... | 606/47 |
| 4,917,082 | 4/1990 | Grossi et al. ............................ | 606/46 |
| 4,920,978 | 5/1990 | Colvin ..................................... | 128/784 |
| 5,078,716 | 1/1992 | Doll ......................................... | 606/47 |
| 5,080,660 | 1/1992 | Buelna .................................... | 606/45 |
| 5,158,087 | 10/1992 | Gatzke ..................................... | 128/662.03 |
| 5,158,561 | 10/1992 | Rydell et al. ............................ | 606/113 |
| 5,196,011 | 3/1993 | Korth et al. ............................. | 606/46 |
| 5,269,782 | 12/1993 | Sutter ...................................... | 606/48 |
| 5,290,282 | 3/1994 | Casscells ................................. | 606/29 |
| 5,312,327 | 5/1994 | Bales et al. ............................. | 604/21 |
| 5,318,564 | 6/1994 | Eggers ..................................... | 606/47 |
| 5,324,288 | 6/1994 | Billings et al. .......................... | 606/45 |
| 5,324,289 | 6/1994 | Eggers ..................................... | 606/48 |
| 5,330,471 | 7/1994 | Eggers ..................................... | 606/48 |
| 5,342,358 | 8/1994 | Daikuzono .............................. | 606/45 |
| 5,376,087 | 12/1994 | Haber et al. ............................. | 606/27 |
| 5,395,363 | 3/1995 | Billings et al. .......................... | 606/41 |
| 5,396,900 | 3/1995 | Slater et al. ............................. | 128/751 |
| 5,403,312 | 4/1995 | Yates et al. .............................. | 606/50 |
| 5,423,813 | 6/1995 | Kaiser et al. ............................ | 606/46 |
| 5,437,665 | 8/1995 | Munro ..................................... | 606/47 |
| 5,456,689 | 10/1995 | Kresch et al. ........................... | 606/180 |
| 5,462,545 | 10/1995 | Wang et al. ............................. | 606/41 |
| 5,484,435 | 1/1996 | Fleenor et al. .......................... | 606/46 |
| 5,486,173 | 1/1996 | Vancaillie ................................ | 606/45 |
| 5,527,331 | 6/1996 | Kresch et al. ........................... | 606/170 |
| 5,531,676 | 7/1996 | Edwards et al. ........................ | 604/22 |
| 5,542,945 | 8/1996 | Fritzsch .................................. | 606/48 |
| 5,558,672 | 9/1996 | Edwards et al. ........................ | 606/41 |
| 5,569,244 | 10/1996 | Hahnen ................................... | 606/46 |
| 5,599,295 | 2/1997 | Rosen et al. ............................ | 604/22 |
| 5,599,345 | 2/1997 | Edwards et al. ........................ | 606/41 |
| 5,599,346 | 2/1997 | Edwards et al. ........................ | 606/41 |
| 5,634,924 | 6/1997 | Turkel et al. ............................ | 606/46 |
| 5,697,281 | 12/1997 | Eggers et al. ........................... | 604/114 |
| 5,697,536 | 12/1997 | Eggers et al. ........................... | 604/114 |
| 5,697,882 | 12/1997 | Eggers et al. ........................... | 604/114 |
| 5,697,909 | 12/1997 | Eggers et al. ........................... | 604/114 |
| 5,810,764 | 9/1998 | Eggers et al. ........................... | 604/23 |
| 5,843,019 | 12/1998 | Eggers et al. ........................... | 604/22 |
| 5,860,951 | 1/1999 | Eggers et al. ........................... | 604/49 |
| 5,871,469 | 2/1999 | Eggers et al. ........................... | 604/114 |
| 5,888,198 | 3/1999 | Eggers et al. ........................... | 604/114 |
| 5,891,095 | 4/1999 | Eggers et al. ........................... | 604/114 |
| 5,902,272 | 5/1999 | Eggers et al. ........................... | 604/114 |
| 5,925,040 | 7/1999 | Nardella et al. ........................ | 606/49 |

FOREIGN PATENT DOCUMENTS 626911  7/1949  United Kingdom ................... 607/147

*Primary Examiner*—Lee Cohen
*Attorney, Agent, or Firm*—Nutter, McClennen & Fish, LLP

[57] ABSTRACT

An electrosurgical instrument includes an electrode assembly having an electrode mechanically interlocked with a non-conductive body to as to form a gap therebetween. In one embodiment, complimentary surface features of the respective electrode and the non-conductive body interlock the components of the electrode assembly. In another embodiment, the electrode assembly includes a generally spherical electrode that is rotatable with respect to a non-conductive hood. A gap is formed between an outer surface of the electrode and an inner surface of the hood.

22 Claims, 8 Drawing Sheets

ELECTROSURGICAL INSTRUMENT

FIELD OF THE INVENTION

The present invention relates to electrosurgical instruments and more particularly to electrosurgical instruments including an electrode with exposed and non-exposed portions.

BACKGROUND OF THE INVENTION

Electrosurgical devices utilize electrical current, such as radio frequency (RF) energy, to cut and to cauterize tissue. The electrical current is delivered via a tissue-contacting portion of the device. The current facilitates a clean tissue cut with little or no bleeding by rapidly heating the tissue without unnecessarily damaging adjacent tissue. Electrosurgical tools can also cauterize tissue separately from or together with a cutting procedure.

Instruments for performing electrosurgery generally include an energy source or generator, an active electrode for delivering electrical energy to tissue to be treated, a return electrode to complete the electrical circuit and conductors for coupling the energy source to the active and return electrodes. A monopolar electrosurgical instrument includes an active electrode for cutting tissue and a remotely located return electrode for providing a current return path. Typically, the return electrode is in contact with a relatively large tissue area, such as a portion of the lower torso, for dispersing exiting current to prevent burning of tissue.

Various types of open and closed surgical procedures utilize electrosurgical devices. Closed surgical procedures include arthroscopic, endoscopic, hysteroscopic, urologic, resectoscopic and laparoscopic procedures. For example, a hysteroscope is used in a closed surgical procedure for treatment of various conditions within a woman's uterine cavity. Typical uses of hysteroscopes include fibroid removal, intrauterine adhesion removal, endometrial ablation and correction of abnormal uterine bleeding.

Some surgical procedures, such as arthroscopic and hysteroscopic procedures, require distension of the surgical area in order to increase visibility at the treatment site or to minimize space constraints. In some instances the surgical area is distended using a fluid.

An electrolyte-free (i.e., hypotonic) distension fluid is typically used in such procedures to prevent the electrical current delivered by the active electrode from dissipating to an ineffective level. However, absorption of excess quantities of hypotonic solution into a patient's bloodstream can alter the patient's electrolyte levels and potentially result in dangerous conditions, including cardiac arrhythmia, brain swelling and even death. The risk of these dangers may cause the surgeon to terminate the procedure before completion. Furthermore, hypotonic solutions are expensive as compared to isotonic solutions.

Although monopolar electrosurgical instruments are useful, there is a need for instruments that are effective in isotonic solutions, especially those instruments useful in closed surgical procedures, such as arthroscopy, endoscopy, hysteroscopy, laparoscopy and resectoscopy.

SUMMARY OF THE INVENTION

The present invention is directed to an electrosurgical instrument having an active electrode with a coated or covered first portion and an exposed second portion which is intended for contacting a treatment site of a patient. The coating or covering is at least partially insulative and serves to direct the delivery of electrosurgical energy from the exposed portion of the active electrode. With this arrangement, the conductive surface area of the electrode in contact with surrounding fluid is reduced, thereby minimizing current dissipation into the surrounding fluid. The electrosurgical instrument of the present invention thus enables the effective use of monopolar electrosurgical tools in an isotonic fluid medium.

In one embodiment, an electrosurgical instrument includes an active electrode selectively coated on a first portion thereof with an insulative or semi-insulative material so as to leave a second, tissue-contacting portion exposed. Generally, a tip portion of the tool is exposed. The geometry of the tissue-contacting or tissue-affecting portion of the active electrode may take various forms depending on the intended application of the electrosurgical instrument. Preferably, the coating material is insulative. More generally however, the coating material has an impedance greater than the impedance of the exposed portion, thus creating a path of lower electrical resistance between the energy source and the exposed portion so as to direct the energy to the exposed portion. In a preferred embodiment, the impedance from the electrode through the coating to the isotonic medium, including any reactance due to parasitic capacitance associated with the coating, is at least one order of magnitude greater than the impedance of the desired current path for an operating frequency of the RF energy source.

In an exemplary embodiment, the active electrode of the electrosurgical instrument has a channel shape, with one or both sides of the channel being blade-like. An intermediate portion of the electrode is coated with an at least semi-insulative material and the blade-like sides of the electrode are exposed. Alternatively, the active electrode can be in the shape of a loop wherein a portion of the surface area of the loop is coated with an insulative or semi-insulative material. In other embodiments, the active electrode has a generally spherical or cylindrical shape with an exposed portion and a coated portion. Other electrode shapes, such as truncated spheres and cylinders, are also possible.

In a further embodiment in accordance with the present invention, an electrosurgical instrument includes an electrode assembly which is pivotally secured to a frame via a coupling mechanism. The electrode assembly includes an electrode having a portion that is coated with an insulative material and an uncoated exposed portion. In one embodiment, the electrode is pivotable from a first position to a second position upon the application of pressure generally along a longitudinal axis of the frame. The pivotable nature of the electrode allows a surgeon to selectively increase the contact area between the exposed portion of the electrode and the tissue.

In still another embodiment, an electrode assembly includes a body formed from a non-conductive material and a conductive coating disposed on a portion of the nonconductive body. The electrode can be formed in a variety of geometries including spherical, hemispherical, cylindrical, and that of a surgical loop. The conductive coating, which is in electrical communication with a source of electrosurgical energy, is effective to treat tissue while the non-conductive body is effective to reduce energy dissipation in an isotonic solution environment.

In a further embodiment in accordance with the present invention, an electrode assembly includes a non-conductive portion or body that is mechanically interlocked with an electrode. The electrode has an outwardly exposed portion that is effective to treat tissue, and a remainder of the electrode surface area is generally covered or shrouded by the non-conductive body. A gap, formed between the electrode and the non-conductive body, in combination with the body provides the desired insulative effect.

In another embodiment, an electrode assembly includes an electrode and a non-conductive hood. The electrode assembly is coupled to a frame such that the electrode is rotatable with respect to the frame while the hood is affixed to the frame. In one embodiment, the electrode is generally spherical with a gap formed between an outer surface of the electrode and an inner surface of the hood. This configuration facilitates contact between the electrode and tissue as the electrode rotates along a tissue site while reducing the dissipation of energy into surrounding isotonic solution.

BRIEF DESCRIPTION OF THE DRAWINGS

The invention will be more fully understood from the following detailed description taken in conjunction with the accompanying drawings, in which.

DETAILED DESCRIPTION OF ILLUSTRATIVE EMBODIMENT

Figure 1:
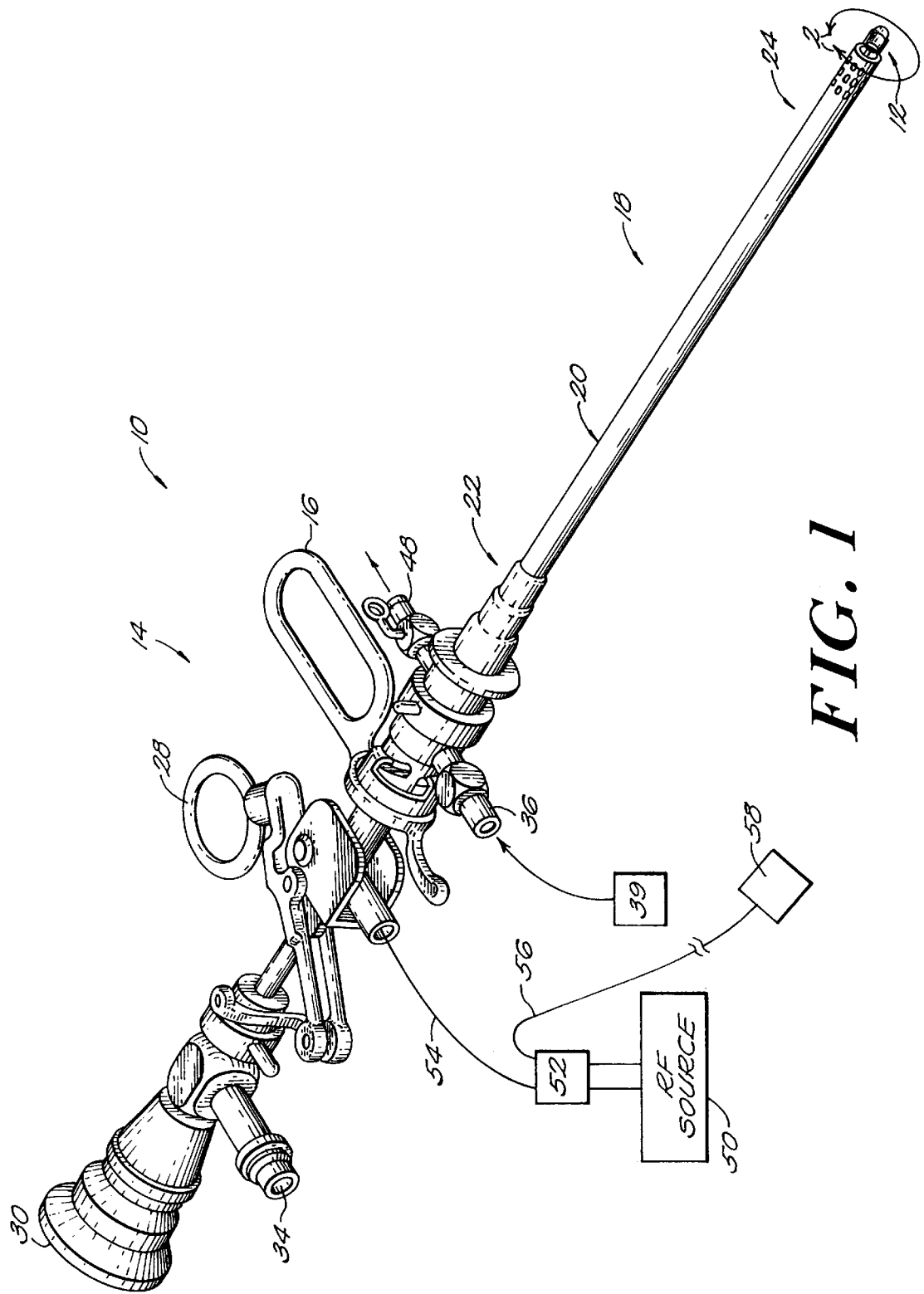
FIG. 1 is a perspective view of a monopolar electrosurgical instrument having a selectively coated active electrode in accordance with the present invention.
Figure 2:
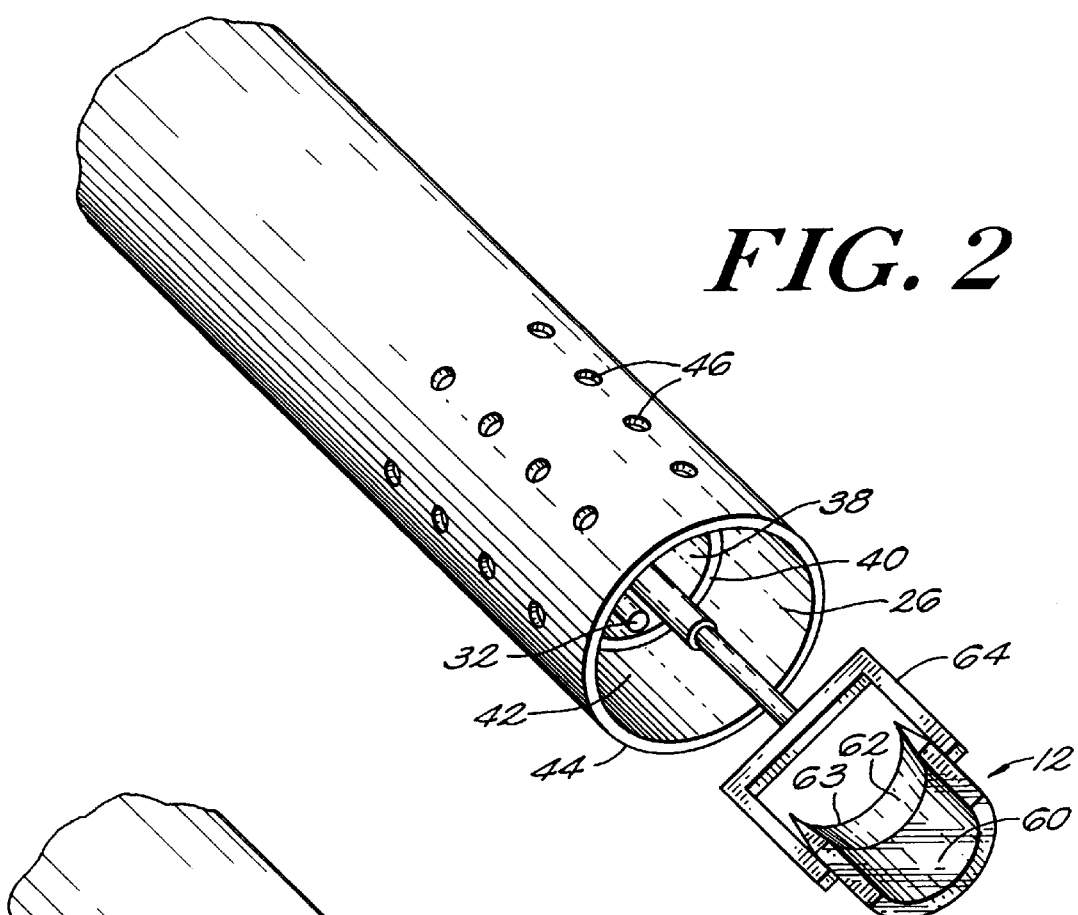
FIG. 2 is an enlarged perspective view of a distal end of the electrosurgical instrument of FIG. 1.
Figure 3:
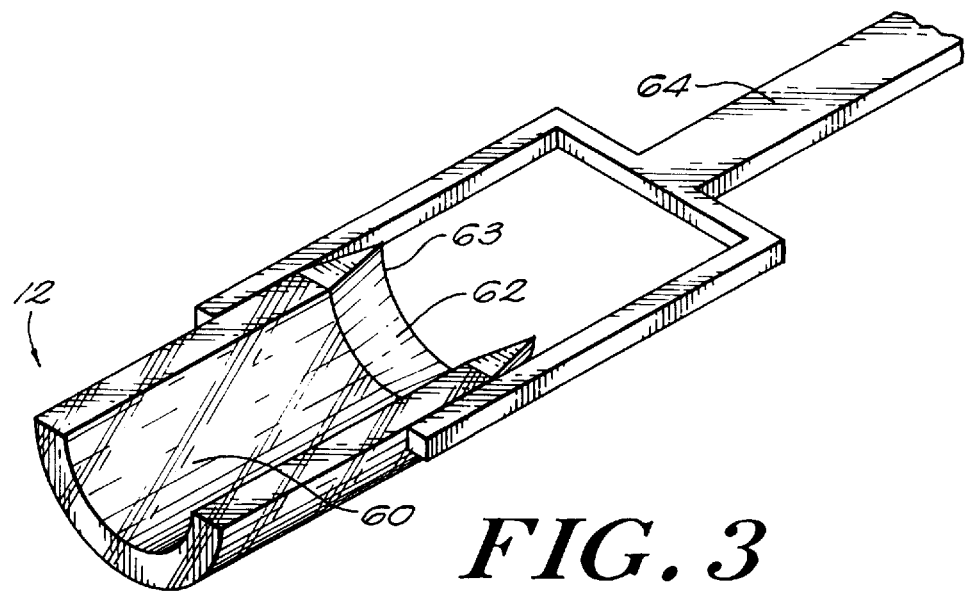
FIG. 3 is an enlarged perspective view of the active electrode of FIG. 1.

Referring to FIGS. 1–3, in which like reference numbers are used to indicate the same elements, an electrosurgical instrument 10 includes a selectively coated active electrode 12 for delivering electrical current to a treatment site of a patient. The instrument is suitable for insertion into the patient in accordance with closed surgery (e.g., arthroscopic, endoscopic, hysteroscopic, urologic, resectoscopic and laparoscopic procedures) or open surgery. The illustrative instrument 10 is a hysteroscope in which the active electrode 12 is intended for insertion into the uterine cavity of a female patient for treatment of various conditions. It will be appreciated however that various types of electrosurgical instruments can be used for other procedures while utilizing and achieving the advantages of the selectively coated electrode described herein.

The instrument 10 includes a proximal portion 14, including a handle 16 for user handling of the instrument in order to guide the electrode 12 into contact with the treatment site, and a forward portion 18. The forward portion 18 includes an elongated probe 20 having a proximal end 22 adjacent to the handle 16 and a distal end 24 from which the active electrode 12 retractably extends. The electrode 12 is capable of being moved along the longitudinal axis of the probe 20 so as to extend through an aperture 26 (FIG. 2) at the distal end 24 of the probe 20 to contact tissue or to be retracted into the end 24 of the probe 20 through the aperture 26. An actuator 28 permits retraction and extension of the electrode 12 via a mechanical coupling within the probe 20.

An optical path within the instrument 10 extends between an eye piece 30 at the rearward portion 14 and a lens 32 at the distal end 24 of the probe 20. The optical path permits the surgeon to view the treatment site. To further facilitate visualization of the treatment site, a light delivery port 34 permits light to be introduced into the optical path.

The electrosurgical instrument 10 is capable of delivering fluid to and collecting fluid from the treatment site. To this end, the instrument 10 includes a fluid input port 36 which is adapted for coupling to an external fluid source 39. The fluid thus introduced into the instrument 10 is directed toward the distal end 24 of the probe 20 via a first, inner fluid channel 38, where the fluid exits the instrument aperture 26. More particularly, the first fluid channel 38 is defined by an inner sheath 40. A second, outer fluid channel 42 between an outer sheath 44 of the probe 20 and the inner sheath 40 serves to collect fluid from the treatment area. To this end, a fluid intake, such as apertures 46 through the outer sheath 44, permit fluid collection. Fluid from the treatment area flows through the second fluid channel 42 toward the proximal end 22 of the probe 20, where the fluid exits the instrument through a fluid output port 48. In one embodiment (FIG. 2), an end of the outer sheath 44 extends beyond an end of the inner sheath 40. In another embodiment (FIG. 2A), the inner sheath 40 extends beyond the end of the outer sheath 44.

An energy source 50, such as a source of radio frequency (RF) energy, provides electrical energy for delivery by the active electrode 12 to the treatment site. More particularly, a control device 52 coupled between the energy source 50 and the instrument 10 permits conventional control of alternating current provided by the source 50, including the ability to turn the energy source on and off as a function of the position of the electrode 12 relative to the treatment site. Conductors 54 and 56 carry the current from or to the energy source, and may be referred to as an active conductor 54 and a return conductor 56. In an exemplary embodiment, the current delivered to the treatment site ranges from 0.1 to 2.0 amps.

The selectively coated electrode of the invention can be a monopolar device, with the return conductor 56 being coupled to a return electrode in the form of a ground pad 58 which is suitable for external attachment to a patient's skin. In particular, the return electrode 58 contacts the patient's body at a remote location relative to the treatment site at which the active electrode 12 is located. The active conductor 54 is coupled to the active electrode 12 through an electrical path within the probe 20.

In another embodiment, at least a portion of the outer sheath and/or inner sheath can form a return electrode for the device. As shown in FIG. 2B, the outer sheath 44 can have a coated portion 47 that is electrically insulated by the coating material and an exposed return electrode portion 49. The return electrode portion can be formed as desired to obtain a desired amount of surface area for the return electrode of the device. This arrangement eliminates or supplements a return electrode in contact with the patient's body.

It is understood that the selectively coated electrode of the invention can be used with a delivery instrument other than the hysteroscope illustrated in FIG. 1. One of ordinary skill in the art will appreciate that the selectively coated electrode can be used with other scope-like instruments, with or without modification of the electrode. Further, the selectively coated electrode of the invention can be used in open surgical procedures without a scope-like delivery device.

The active electrode 12 includes a first portion 60 covered with a coating. A second, tissue-affecting portion 62 of the active electrode remains exposed. The tissue-affecting portion of the electrode is understood to be the portion of the electrode from which current is delivered to tissue. This portion of the electrode is largely responsible for cutting and/or cauterizing tissue that it contacts. A frame 64 coupled to the active electrode 12 provides a mechanism for mechanically supporting the electrode 12. Further, the frame 64 may be conductive and may provide a mechanism for coupling electrical energy from a source (not shown) to the tissue-affecting portion 62 of the electrode. The conductive frame should be coated, at least in part, with an insulative coating to reduce energy dissipation in the surrounding isotonic solution. In a further embodiment, the frame is a hollow, non-conductive member having a conductive path therein to allow the electrosurgical generator to energize the active electrode.

In one embodiment, illustrated in FIGS. 2 and 3, the electrode 12 is substantially channel-shaped, with the tissue-affecting portion 62 terminating at a sharp, blade-like tip 63. The coating material can extend over virtually the entire surface of the electrode, except for the sharpened edge of the blade-like tip 63. The smaller the surface area of the non-coated portion of the electrode, the greater will be the density of current emanating from the electrode. This feature increases the ability of the electrode to deliver current directly to the target tissue with little or no current dissipation in an isotonic fluid environment or to non-target tissue.

While the coating effectively insulates the covered first portion 60 of the active electrode, there is a parasitic capacitance formed on the covered first portion due to the coating. The insulative, or partially insulative, coating acts as a dielectric between conductive isotonic solution and the first portion 60 of the electrode producing a capacitive effect. The parasitic capacitance has a reactance associated therewith that forms a portion of the impedance through the solution and the coated first portion 60 of the active electrode. Preferably, this impedance is much greater than the impedance between the exposed tissue-affecting portion 62 of the active electrode and the solution or tissue.

In a preferred embodiment, the impedance associated with the coated first portion 60 of the electrode is at least one order of magnitude greater than the impedance of the desired current path from the tissue affecting portion 62 of the electrode to tissue and/or isotonic solution at the desired operating frequency of the RF generator. As is understood by one of ordinary skill in the art, the reactance due to the parasitic capacitance of the coated first portion of the electrode, and therefore the impedance, is frequency dependent. Thus, impedances are measured at the operating frequency of the RF energy source 50. The impedance through the coating can be chosen to be much greater than the impedance of the desired current path by adjusting the thickness of the coating material. To provide the preferred much greater impedance through the coated portion of the electrode for a given operating frequency, a coating thickness is selected to obtain the desired impedance value.

In one embodiment, the coating material is an insulative or partly insulative material. It is understood that insulative, as used herein, is to be construed broadly. In an exemplary embodiment, the coating is a medical grade ceramic material, such as aluminum oxide. Other coating materials include ceramics (e.g., glass, aluminum-silicate, alumina, or boron), non-conductive epoxy, ceramic adhesive, glass enamels, glass-filled polymers, polysulfones, polytetrafluoroethylene, polysiloxanes, silicones, polyetheretherketone, Parylene, and Kevlar. It will be appreciated by those of ordinary skill in the art that the thickness of the coating material can be readily varied. In a preferred embodiment, however, the thickness is in the range of about 2 microns to about 150 microns. The ceramic coating can be applied by vacuum chamber deposition or by electrostatically spraying a ceramic material and curing the coating at a suitable temperature. Other coating techniques will be apparent to those having ordinary skill in the art.

Figure 3A:
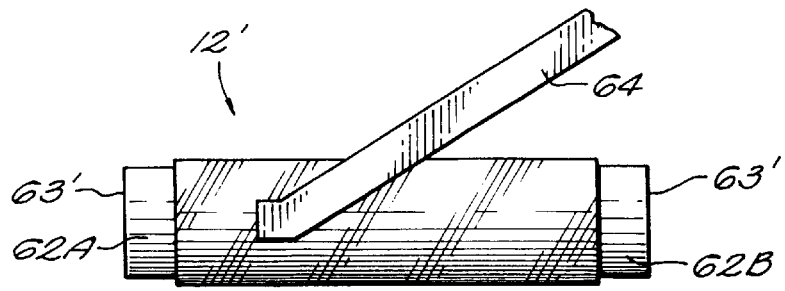
FIG. 3A is an alternative embodiment of the active electrode of FIG. 3.

In a further embodiment shown in FIG. 3A, the electrode has dual blade-like edges 63', with an insulative coating in the area between the edges. This dual-edged arrangement is well suited for certain procedures involving scraping of tissue. Many other electrode geometrics are also possible. The electrodes further may or may not have sharpened blade-like edges. An important feature of the invention is to maximize the coated area of the electrode while minimizing the non-coated, tissue-affecting portion of the electrode. One of ordinary skill in the art will appreciate that further alternative electrode geometries can be used without departing from the scope of the invention.

In other embodiments, the coating material is semi-insulative. Suitable semi-insulative coatings include those having an impedance greater than that of the exposed portion of the electrode, so as to provide a path of lower electrical resistance between the energy source and the exposed portion 62 as compared to the path between the energy-source and the coated portion 60. Thus, current is directed toward the exposed tissue-contacting portion 62 of the electrode in order to enhance the electrosurgical effect of the device. This energy focusing aspect of the instrument further serves to render the instrument suitable for use in an isotonic fluid medium by reducing the conductive surface area of the active electrode. In addition, by limiting the surface area of the exposed portion 62 of the electrode, a glow associated with the use of an energized electrode in an isotonic solution is reduced. This enhances the field of vision of the surgeon when treating tissue with the electrode.

In an illustrative embodiment, the electrode 60 is tungsten, but other biologically compatible materials having suitable conductivity and strength can be used. Examples of suitable materials include stainless steel, tungsten, titanium, platinum, silver, gold, brass, nickel-titanium alloys and other biocompatible metals.

Figure 2A:
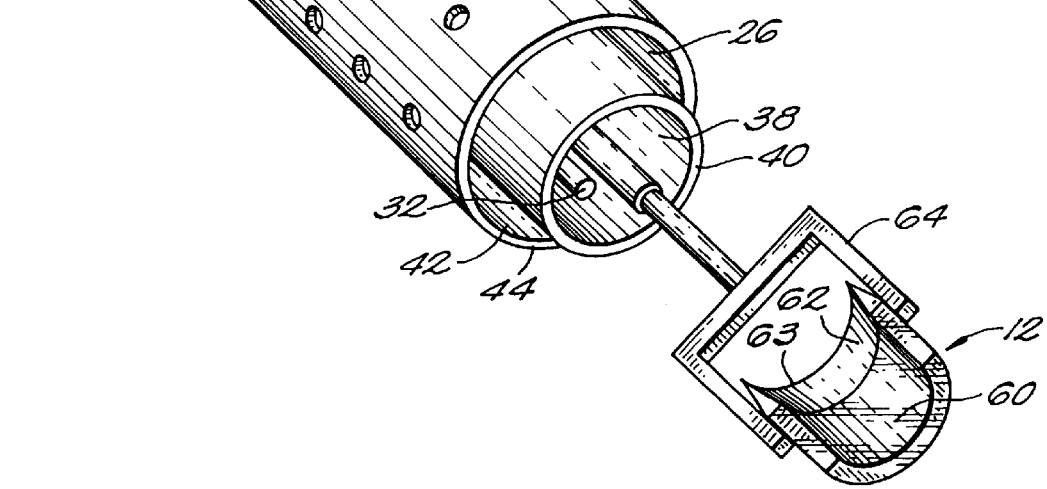
FIG. 2A is an alternative embodiment of the electrosurgical instrument of FIG. 2.
Figure 2B:
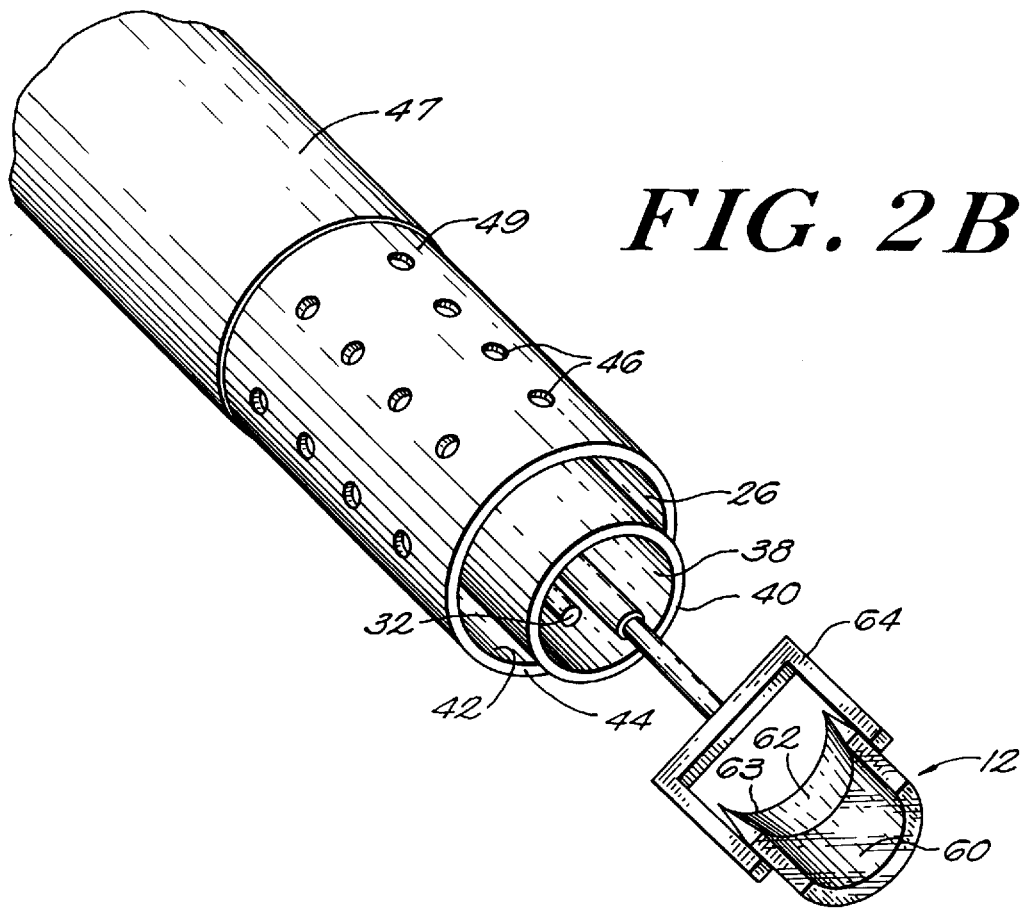
FIG. 2B is a further embodiment of the electrosurgical instrument of FIG. 2.
Figure 4A:
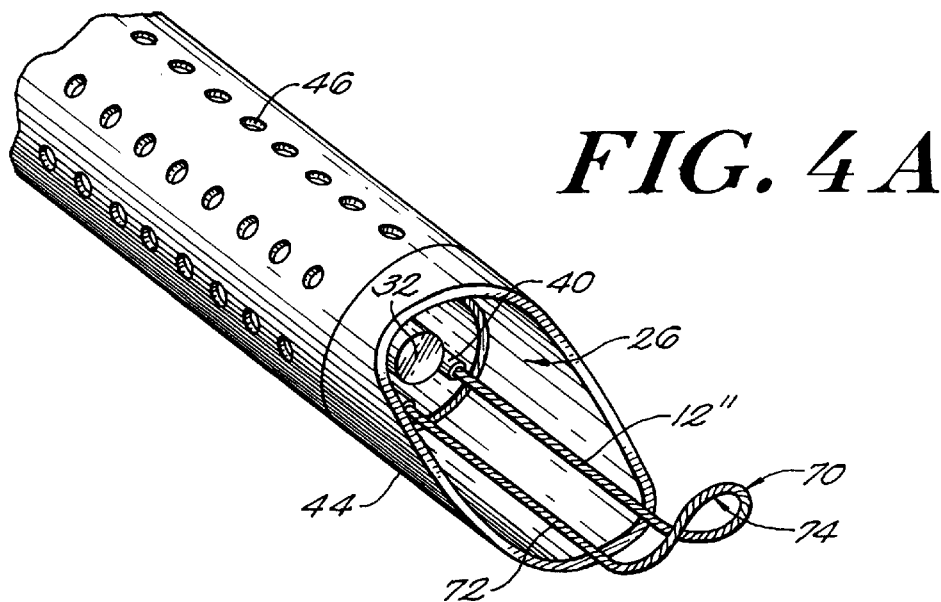
FIG. 4A is another embodiment of the electrosurgical instrument of FIG. 2.

FIG. 4A is another embodiment of a monopolar electrosurgical instrument having an active electrode 12" in the form of a loop 70 that extends from an inner sheath 40 that is disposed with an outer sheath as discussed in conjunction with FIG. 2A. The loop 70 includes a coated portion 72 and an exposed tissue-affecting portion 74. The tissue-affecting portion 74 cuts and/or cauterizes tissue under the control of an operator, such as a surgeon. Current density is maximized at the tissue-affecting portion 74 of the loop so that current dissipation in isotonic solution and non-target tissue is minimized.

Figure 4B:
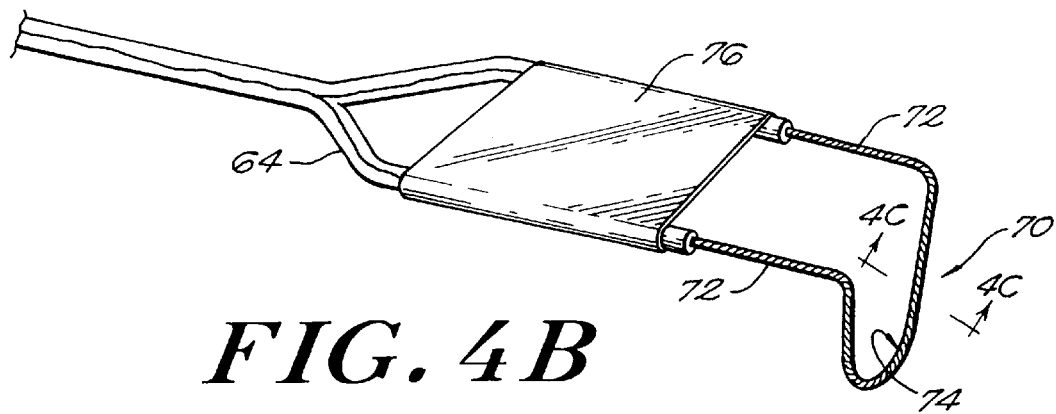
FIG. 4B is a further embodiment of the distal end of the electrosurgical instrument of FIG. 4A.

FIG. 4B is a further embodiment of an active electrode 12" in the form of a loop 70 having a coated first portion 72 and an exposed tissue-affecting portion 74. The loop 70 extends from a frame 64 that supports the loop during use. A return electrode 76 is electrically insulated from the loop and is disposed on the frame to provide a return path for current from the loop.

Figure 4C:
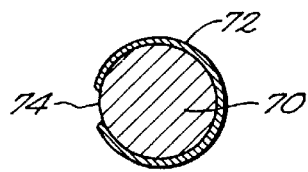
FIG. 4C is a sectional view of a portion of the electrosurgical instrument of FIG. 4B at lines 4C—4C.

Various coating patterns can be used. Ideally, only a minimal portion of the blade should remain uncoated. Preferably the portion of the loop that is to be in contact with tissue should remain uncoated while the remainder of the loop, that is to be in contact with an isotonic solution, should be coated. FIG. 4C illustrates an example of a coating pattern in which virtually the entire loop is coated except for a rear-facing circumferential portion 74. Other coating patterns may be used as well. For example, the entire loop can be coated, except for an uncoated distal-most end.

Figure 5A:
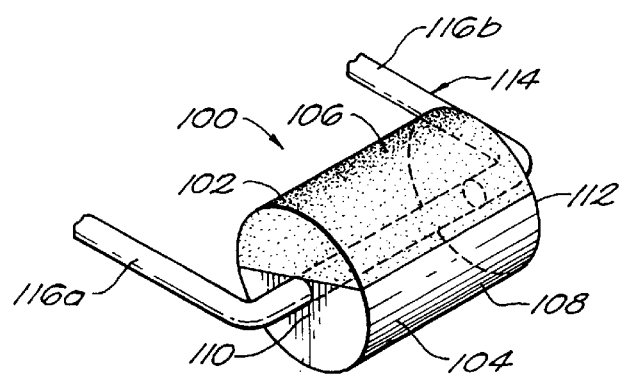
FIG. 5A is a perspective view of another embodiment of an active electrode in accordance with the present invention.

FIG. 5A shows another embodiment of an active electrode 100 having an insulative coating 102 disposed on a portion of an outer surface 104 of the electrode so as to form a coated portion 106 and an non-coated exposed portion 108. It is understood that the apportionment between the coated portion 106 and the exposed portion 108 can vary. In general, the exposed portion 108 of the electrode should be minimized to reduce energy dissipation into a conductive solution while providing a desired surface area for contact between the electrode and the tissue.

The electrode 100 can be formed in a variety of geometries including cylindrical, spherical, arcuate, convex, and hemispherical. In one embodiment, the electrode 100 is generally cylindrical with opposite first and second ends 110,112. A frame 114 includes a first structural member 116a coupled to the first end 110 of the electrode and a second structural member 116b coupled to the second end 112. The structural members 116 are affixed to the first and second ends 110,112 such that the electrode 100 remains in a predetermined position with respect to the structural members 116a,b. It is understood that the frame 114 can be affixed to the electrode 100 at a range of angles depending upon the particular orientation of the target tissue in relation to the exposed portion 108 of the electrode.

Figure 5B:
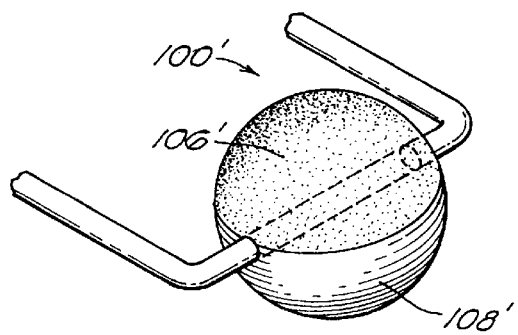
FIG. 5B is a perspective view of a further embodiment of an active electrode in accordance with the present invention.

FIG. 5B shows an alternative embodiment of the electrode 100 of FIG. 5A wherein the electrode 100' has a generally spherical shape. The electrode 100' has a portion 106' coated with an insulative material and an exposed portion 108' for treating tissue.

Figure 6A:
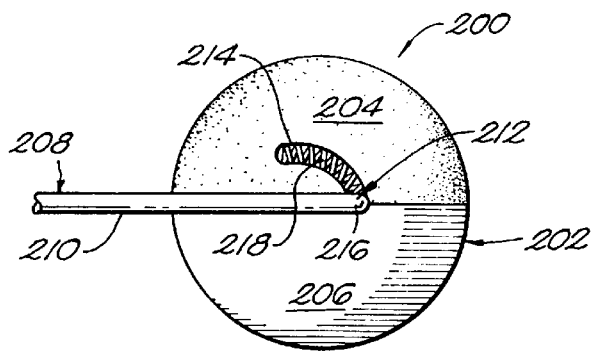
FIG. 6A is a side view of an electrode assembly in accordance with the present invention with the assembly having an electrode shown in a first position.
Figure 6B:
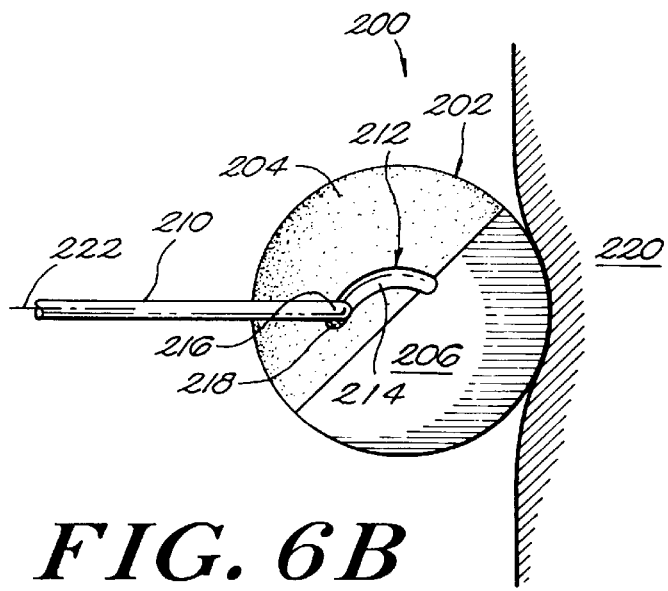
FIG. 6B is a side view of the electrode assembly of FIG. 6B with the electrode shown in second position.
Figure 6C:
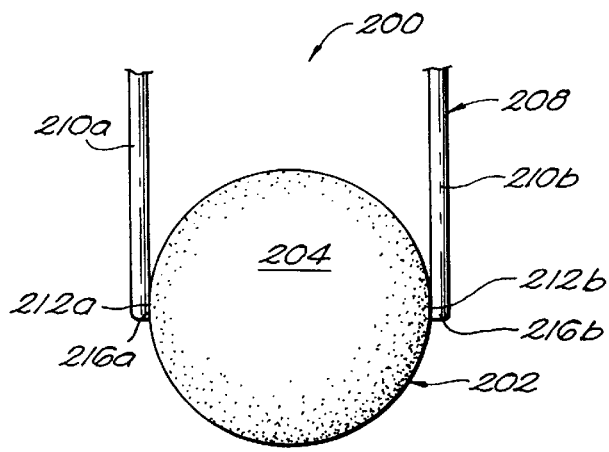
FIG. 6C is a top view of the electrode assembly of FIG. 6A.

In FIGS. 6A–C, an electrode assembly 200 is shown having an electrode 202 which is movable between a first position (FIG. 6A) and a second position (FIG. 6B). The electrode 202 has a portion 204 coated with an insulative material and an exposed portion 206 adapted for treating tissue. In one embodiment, a frame 208 includes first and second structural members 210a,b pivotally coupled to opposite locations on the electrode 202 via first and second coupling mechanisms 212a,b.

The coupling mechanisms 212 can be formed from a variety of mechanisms that allow selective movement of the electrode 202 with respect to the frame 208. Exemplary mechanisms include positive and negative surface features, hinges and pivoting structures. It is understood that the electrode 202 and/or the frame 208 can provide the pivoting action of the electrode assembly. In one embodiment, the coupling mechanisms 212a,b include an arcuate groove 214 formed in the electrode 202 into which distal tips 216a,b of the structural members 210a,b are inserted. Electrical contact between the distal tips 216a,b and the electrode is maintained to provide a constant flow of energy to the electrode. The electrode 202 rotates between the first position (FIG. 6A) and the second position (FIG. 6B) as the distal tips 216 move within the grooves 214. The electrode 202 can be biased to the first (or second) position with a biasing member 218, such as a spring. The amount that the electrode 202 can rotate with respect to the frame 208 can range from about fifteen degrees to about ninety degrees.

The pivotal feature of the electrode 202 allows a surgeon to control the position of the exposed portion 206 of the electrode with respect to tissue 220. That is, with the application of pressure generally along a longitudinal axis 222 of the structural members 210, the exposed portion 206 of the electrode rotates so as to increase the contact area between the tissue 220 and the exposed portion 206 of the electrode. Thus, the pivotal feature of the electrode assembly 200 enhances the ability of a surgeon to selectively treat tissue with the exposed portion 206 of the electrode. For example, the pivoting electrode assembly is well-suited for treating endometrium tissue with a dabbing type motion.

Figure 7:
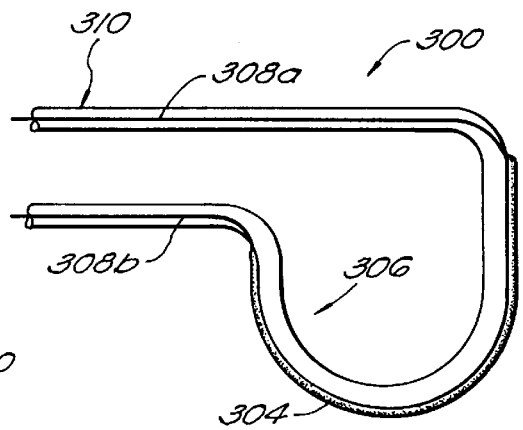
FIG. 7 is a perspective view of an electrode assembly in accordance with the present invention, the assembly having a non-conductive body in the form of a surgical loop and a conductive coating.

FIG. 7 illustrates another embodiment of an electrode assembly 300 in accordance with the present invention. The assembly 300 includes an electrode formed from a coating 304, which is made from a conductive material, disposed on a body 306, which is formed from a non-conductive material. Coupled to the conductive coating 304 are conductors 308a,b extending along a frame 310 to an electrosurgical RF energy source 50 (FIG. 1).

The electrode assembly 300 can be formed in a variety of configurations such as surgical loops, spheres, cylinders, and hemispheres. In one embodiment, the electrode assembly 300, including the non-conductive body 306 and conductive coating 304, is configured as a surgical loop. The conductive coating 304 is selectively applied to the body 306 so as to provide a tissue-cutting electrode that is effective to minimize energy dissipation in an isotonic solution. In general, the conductive coating 304 should be of sufficient size to conduct operational current levels without excessive heating of the coating 304 and/or the adjacent body 306. An exemplary thickness range for the coating 304 is from about 0.001 inch to about 0.100 inch. It is understood that a relatively thick coating increases durability.

The non-conductive body 306 can be formed from suitable materials that are sufficiently strong and rigid to resist breaking as pressure is applied to the electrode assembly during use. Exemplary materials for the non-conductive body include ceramics (e.g., glass, aluminum-silicate, alumina, or boron), non-conductive epoxy, ceramic adhesive, glass enamels, glass-filled polymers, polysulfones, polytetrafluoroethylene, polysiloxanes, silicones, polyetheretherketone, Parylene, and Kevlar.

The conductive coating 304 is formed from a material that provides a suitable circuit path for the applied electrosurgical energy. The conductive coating can be formed from a variety of materials including metals such as stainless steel, tungsten, titanium, platinum, silver, gold, brass, nickel-titanium alloys and other biocompatible metals.

Figure 8A:
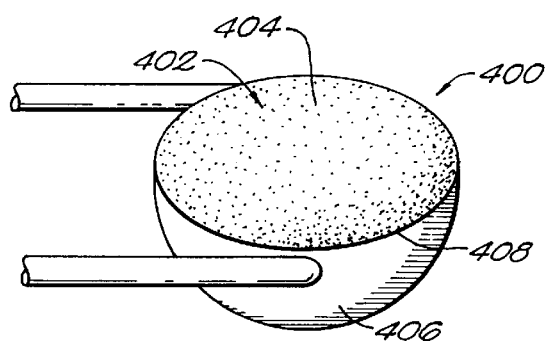
FIG. 8A is a perspective view of another embodiment of an electrode assembly in accordance with the present invention, the assembly having a hemispherical non-conductive body and a conductive coating.

In FIG. 8A, an electrode assembly 400 has an electrode 402 formed from a conductive coating 404 which covers a portion of a body 406 formed from a non-conductive material. In one embodiment, the non-conductive body 406 has a hemispherical shape with the conductive coating 404 formed on a planar surface 408 of the body. The hemispherical geometry of the electrode assembly 400 enhances the visual field of the surgeon by reducing the overall size of the electrode assembly as compared with spherical electrodes and the like.

Figure 8B:
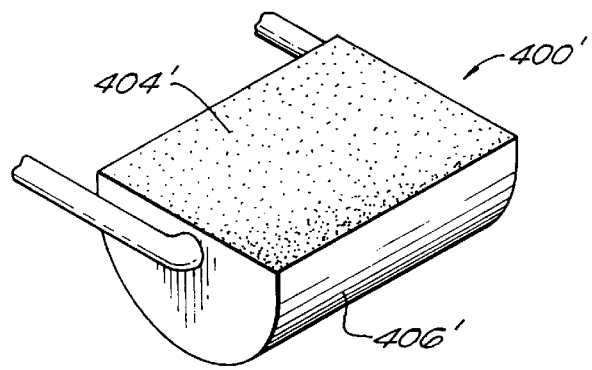
FIG. 8B is a perspective view of a further embodiment of an electrode assembly in accordance with the present invention, the assembly having a non-conductive body with a generally hemi-cylindrical shape and a conductive coating.
Figure 8C:
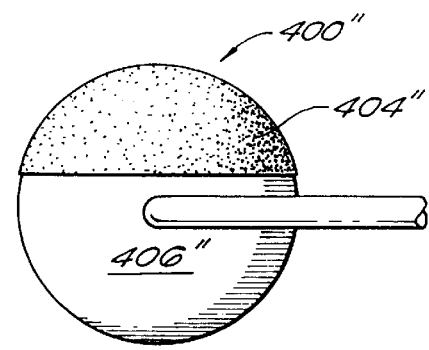
FIG. 8C is a perspective view of a still further embodiment of an electrode assembly in accordance with the present invention, the assembly having a generally spherical non-conductive body and a conductive coating.

FIG. 8B shows an alternate embodiment of an electrode assembly 400' having a cylindrical geometry with a conductive coating 404' disposed on a non-conductive body 406'. And FIG. 8C shows an electrode assembly 400" having a generally spherical shape with a conductive coating 404" covering a portion of a non-conductive body 406". In an exemplary embodiment, the coating ranges in thickness from about 0.001 inch to about 0.100 inch.

It is understood that the conductive coatings 404 are coupled to an electrosurgical RF generator 50 like that shown in FIG. 1 via conductors 308 like those shown in FIG. 7.

In further embodiments of the invention described below, an electrode assembly includes an active electrode which is mechanically interlocked with a non-conductive body or hood. In general, the electrode and the hood are disposed in proximity with each other so as to form a gap. The hood and gap combine to provide the desired insulative effect that is effective to minimize current dissipation from a portion of the electrode that does not contact tissue.

Figure 9:
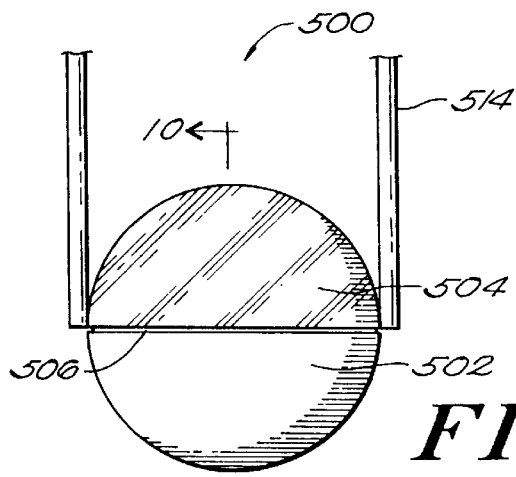
FIG. 9 is a top view of a an electrode assembly in accordance with the present invention, the assembly having an electrode mechanically interlocked with a non-conductive body.
Figure 10:
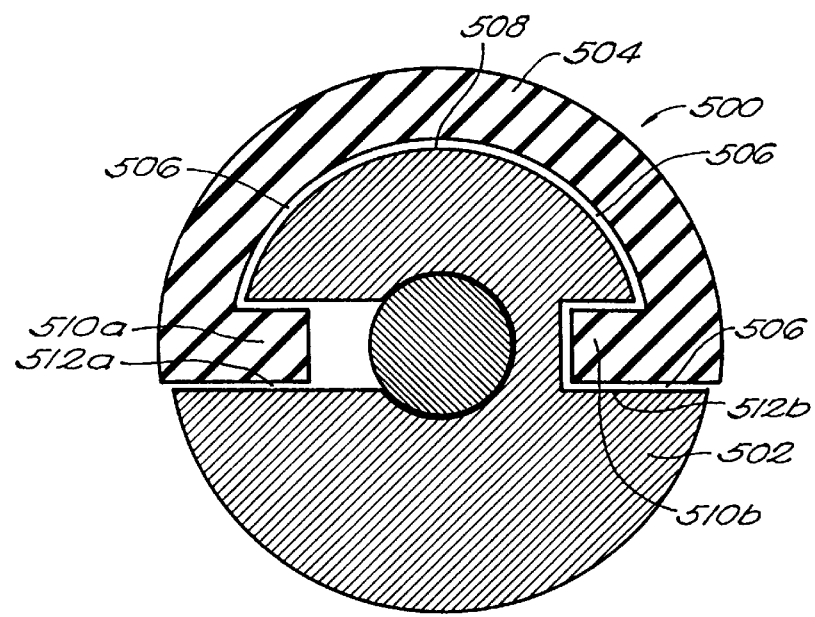
FIG. 10 is a cross-sectional view of the electrode assembly of FIG. 9 along lines 10—10.

FIGS. 9–10 show an electrode assembly 500 including an electrode 502 for treating tissue and a non-conductive portion or body 504 for reducing energy dissipation into an isotonic solution. The non-conductive body 504 is mechanically coupled to the electrode 502 so as to form a gap 506. As used herein, mechanical coupling or interlocking refers to structural features that position the non-conductive body 504 with respect to the electrode 502. That is, the non-conductive body 504 does not adhere to the electrode 502. Further, it is understood that the gap 506 can vary in distance from substantially zero to about 0.08 inch. The mechanism used to couple the body 504 to the electrode 502 can be formed from a variety of structures. Exemplary mechanisms include complementary surface features, interference engagements, snap-fits, adhesives, insert molding, and heat shrinking. In general, the mechanical coupling mechanism should retain the non-conductive body 504 in close proximity with an outer surface 508 of the electrode 502 so as to maintain the gap 506. It is understood that the gap 506 between the electrode 502 and the body 504 can be continuous or discontinuous and uniform or non-uniform. For example, the electrode and/or the non-conductive body may have an irregular surface contour which includes grooves, dimples and other surface features that generate a non-uniform gap.

In one embodiment, the non-conductive body 504 includes first and second surface features 510a,b in the form of protrusions that are sized to fit within complementary channels 512a,b formed in the outer surface 508 of the electrode. The protrusions 510 securely engage the body 504 to the electrode 502 and form the gap 506 therebetween.

It is understood that the electrode assembly 500 can be coupled to a frame 514 such that the electrode assembly is in a fixed position (FIGS. 9–10), or so that the electrode assembly can rotate with respect to the frame 514 (FIG. 11) as pressure is applied to maintain contact between the frame and the electrode. It is further understood that energy flows to the electrode 502 via conductors (not shown) that extend along the frame 514 and axle to a source of electrosurgical energy.

Figure 11:
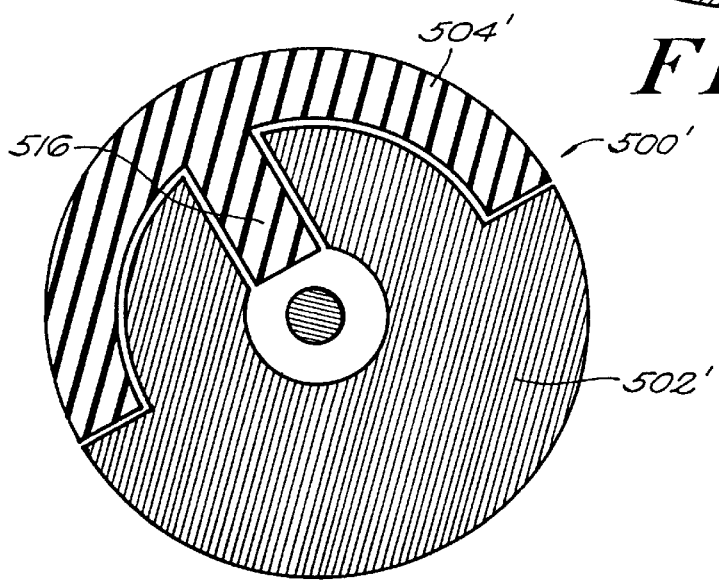
FIG. 11 is a cross-sectional view of an alternative embodiment of the electrode assembly of FIG. 10.

FIG. 11 shows an alternative embodiment of an electrode assembly 500' having an electrode 502' and a non-conductive body 504' having a member 516 protruding inwardly to a central portion of the electrode 502'. The protruding member 516 is effective to securely engage the non-conductive body 504' to the electrode 502' by means of mechanical interference.

In use, a surgeon positions the electrode 502 in contact with tissue as desired. Although some saline or other isotonic fluid may enter the gap 506, the fluid is quickly transformed to steam due to the high temperature of the electrode 502. Relatively little energy will be dissipated in the steam as compared with isotonic solution. In addition, tissue debris, such as desiccated tissue, which enters the gap 506 is generally insulative. Thus, the non-conductive body 504 provides the desired insulative effect without intimate contact with the electrode.

The gap 506 also provides space for thermal expansion of the metallic electrode 502 as the temperature of the electrode increases during use. The non-conductive body 504 can be sized to accommodate thermal expansion of the electrode to achieve a desired distance for the gap 506. Alternatively, the non-conductive body 504 can be formed so as to be slightly undersized upon full thermal expansion of the electrode 502 so as to capture the electrode during use. It is understood that the apportionment of the electrode assembly 500 between the electrode 502 and the non-conductive body 504 can vary depending upon the requirements of a particular application. In general, the electrode 502 should have a geometry adapted for treating a selected area of tissue at a desired energy level.

Exemplary materials for the non-conductive body 504 include ceramics (e. g., glass, aluminum-silicate, alumina, or boron), non-conductive epoxy, ceramic adhesive, glass enamels, glass-filled polymers, polysulfones, polytetrafluoroethylene, polysiloxanes, silicones, polyetheretherketone, Parylene, and Kevlar.

Figure 12A:
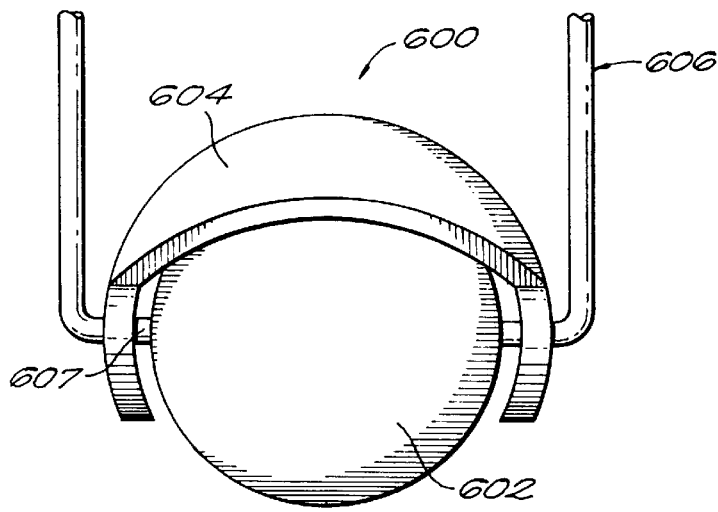
FIG. 12A is a front view of a further embodiment of an electrode assembly in accordance with the present invention, the assembly having an electrode that is rotatable with respect to a non-conductive hood.
Figure 12B:
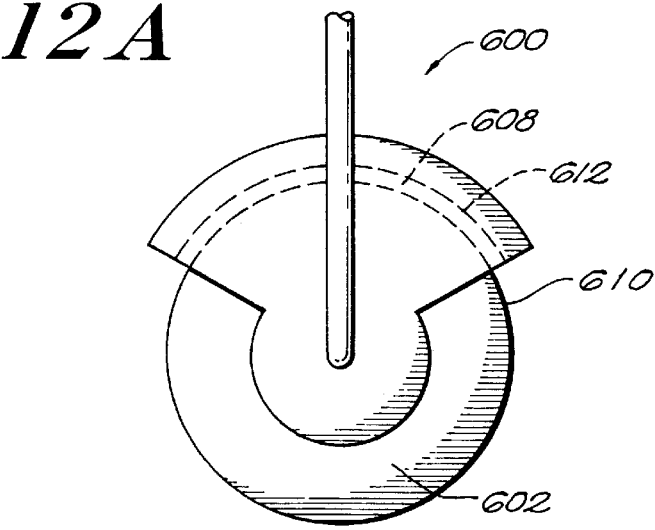
FIG. 12B is a side view of the electrode assembly of FIG. 12A.

FIGS. 12A–B show an electrode assembly 600 having an electrode 602 that is rotatable with respect to a non-conductive hood 604 and a frame 606. The hood 604 is affixed to the frame 606 while the electrode 602 is rotatably secured to the frame 606. The electrode 602 is electrically coupled to an axle portion 607 of the frame to provide a path for RF energy to flow to the electrode. A gap 608 is formed between an outer surface 610 of the electrode and an inner surface 612 of the hood. The gap 608 and non-conductive hood 604 combine to provide an insulative effect for a covered portion of the electrode 602 as the electrode assembly 600 is rolled along a tissue site in an isotonic solution environment.

Figure 12C:
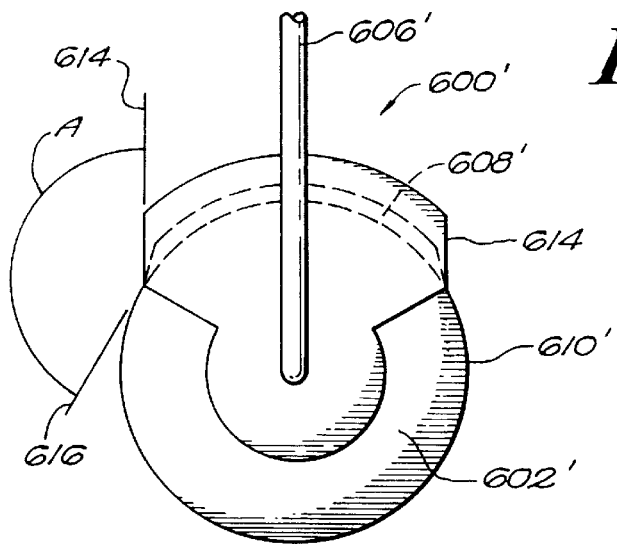
FIG. 12C is a side view of an alternative embodiment of the electrode assembly of FIG. 12B.

FIG. 12C shows an alternative embodiment of an electrode assembly 600' having a hood 604' with a lateral surface 614 that forms an obtuse angle A with respect to the outer surface 610' of the electrode 602'. The angle A can vary from about ninety degrees to about 180 degrees with respect to a tangent 616 to the electrode 602'. As shown, the gap 608' can also narrow proximate the lateral surface 614, such as to a distance between about 0.001 inch to about 0.010 inch. The lateral surface 614 of the hood is effective to scrape off tissue adhering to the electrode as it rotates.

It is understood that the dimensions of the electrode assembly 600 components can vary. In an exemplary embodiment, the electrode 602 has a diameter in the range from about 2 to about 5 millimeters and the hood 604 has a thickness in the range from about 0.01 inch to about 0.08 inch. It is further understood that the amount of uncovered electrode can vary depending upon the particular application. In general, the uncovered portion of the electrode surface area can range from ten to ninety percent.

One of ordinary skill in the art will appreciate that the invention enables a monopolar electrosurgical tool (i.e., one that utilizes a remote ground pad to complete the electrical circuit) to be used in an environment that includes an isotonic fluid. Generally, monopolar electrosurgical devices deliver current to tissue in a non-focused manner such that the current is passed to target tissue as well as other non-target tissue in the vicinity of the electrode. As noted above, this can present a problem in closed surgical procedures that involve the use of a fluid medium. The tendency of conventional monopolar tools to dissipate current generally precludes their use in an isotonic fluid medium. However, the present invention, which permits the focused delivery of electrosurgical energy, with little or no current dissipation outside of target tissue, enables the use of a monopolar electrosurgical instrument in an isotonic fluid medium.

Generally, an isotonic fluid medium is understood to be one having an osmolarity in the range of about 260 or 295 milliosmols. Examples of suitable isotonic fluids are saline and Ringer's lactate.

The foregoing description of the illustrative embodiments of the invention is presented to indicate the range of constructions to which the invention applies. Variations in the physical architecture and dimensions of the invention will be apparent to those having ordinary skill in the art based upon the disclosure herein.

What is claimed is:

1. An electrosurgical device, comprising:

a frame having a proximal end and a distal end; and an electrode assembly coupled to the distal end of the frame, the electrode assembly including an electrode; and a non-conductive body positioned and mechanically interlocked with the electrode such that a gap is formed between the electrode and the non-conductive body effective in use to substantially reduce current dissipation into an electrolyte solution from a portion of the electrode not contacting tissue.

2. The device according to claim 1, wherein the electrode has a first surface feature and the non-conductive body has a second surface feature such that the first and second surface features are effective to mechanically interlock the electrode and the non-conductive body.

3. The device according to claim 1, wherein the electrode assembly is fixed in position with respect to the frame.

4. The device according to claim 1, wherein the electrode assembly is generally spherical.

5. The device according to claim 1, wherein the electrode assembly is rotatable with respect to the frame.

6. The device according to claim 1, wherein the electrode is generally spherical.

7. The device according to claim 1, wherein the electrode is rotatable with respect to the non-conductive body.

8. The device according to claim 7, wherein the non-conductive body is formed from a material selected from the group consisting of ceramics, glass, aluminum-silicate, alumina, boron, non-conductive epoxy, ceramic adhesive, glass enamels, glass-filled polymers, polysulfones, polytetrafluoroethylene, polysiloxanes, silicones, polyetheretherketone, Parylene, and Kevlar.

9. The device according to claim 1, wherein the electrode assembly has a diameter in the range from about two millimeters to about five millimeters.

10. The device according to claim 1, wherein the gap has a distance of less than about 0.08 inch.

11. The device according to claim 10, wherein the gap decreases due to thermal expansion of the electrode during use.

12. The device according to claim 1, wherein the electrode is generally spherical and the non-conductive body covers from about ten percent to about ninety percent of an outer surface of the electrode.

13. A monopolar electrosurgical device, comprising:

a frame;

an electrode assembly affixed to the frame, the electrode assembly including an electrode that is effective to treat tissue and a non-conductive body that is mechanically interlocked with the electrode such that a gap is formed between the electrode and the non-conductive body effective in use to substantially reduce current dissipation into an electrolyte solution from a portion of the electrode not contacting tissue.

14. The device according to claim 13, wherein the non-conductive body includes at least one surface feature that is matable to the electrode.

15. The device according to claim 13, wherein the electrode includes at least one surface feature that is matable to the non-conductive body.

16. The device according to claim 13, wherein the gap is less than about 0.08 inch.

17. A monopolar electrosurgical device, comprising:

a frame;

an electrode assembly coupled to the frame, the electrode assembly including a generally spherical electrode rotatably coupled to the frame and a non-conductive hood affixed to the frame such that a gap is formed between an outer surface of the electrode and an inner surface of the hood effective in use to substantially reduce current dissipation into an electrolyte solution from a portion of the electrode not contacting tissue.

18. The device according to claim 17, wherein the gap is less than about 0.08 inch.

19. The device according to claim 17, wherein the gap is generally uniform.

20. The device according to claim 17, wherein the hood includes a lateral surface that is effective to scrape tissue from the electrode as the electrode rotates.

21. The device according to claim 20, wherein the gap narrows proximate the lateral surface of the hood.

22. The device according to claim 20, wherein the lateral surface forms an angle of greater than ninety degrees with respect to a tangent to the electrode.

* * * * *